US00PP37353P2

(12) United States Plant Patent
Neu

(10) Patent No.: US PP37,353 P2
(45) Date of Patent: Mar. 31, 2026

(54) *PELARGONIUM* PLANT NAMED 'KLEPZ24810'

(50) Latin Name: *Pelargonium zonale* x *peltatum*
Varietal Denomination: KLEPZ24810

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 19/179,381

(22) Filed: Apr. 15, 2025

(51) Int. Cl.
*A01H 5/02* (2018.01)
*A01H 6/42* (2018.01)

(52) U.S. Cl.
USPC ..... Plt./328

(58) Field of Classification Search
USPC ..... Plt./328, 324
CPC . A01H 5/02; A01H 5/00; A01H 6/425; A01H 6/42
See application file for complete search history.

(56) References Cited

PUBLICATIONS

Facebook Selecta One Post 2024, retrieved on Aug. 11, 2025 at https://www.facebook.com/selectaone1/posts/pink-flower-power-our-new-pelargonium-nelia-makes-a-perfect-match-to-pelargonium/1012798370849745/, one page. (Year: 2024).*
Selecta One Spring Annuals Trixi 2024/2025, retrieved on Aug. 11, 2025 at https://josvainiugeles.lt/wp-content/uploads/2024/09/Selecta-Annuals-2025.pdf, pp. 1-3, 72-73 (3 pp. total). (Year: 2025).*

* cited by examiner

*Primary Examiner* — June Hwu
(74) *Attorney, Agent, or Firm* — Weatherly IP Solutions, LLC; James M. Weatherly

(57) ABSTRACT

A new *Pelargonium* plant particularly distinguished by pink flowers with small markings; dark green leaves; and very weak leaf zonation, is disclosed.

1 Drawing Sheet

Genus and species: *Pelargonium zonale* x *peltatum.*
Variety denomination: 'KLEPZ24810'.

BACKGROUND OF THE NEW PLANT

The present invention comprises a new and distinct variety of *Pelargonium*, botanically known as *Pelargonium zonale* x *peltatum* and hereinafter referred to by the variety name 'KLEPZ24810'. 'KLEPZ24810' originated from a controlled cross in July 2019 in Juja, Kenya between the proprietary female *Pelargonium* variety 'PZ-2017-7461' (unpatented) and the commercial male *Pelargonium* variety CALLIOPE® L Dark Red (patent status unknown).

Seeds from the controlled cross were obtained. The seeds were sown and plants were grown for evaluation. A single plant was selected in June 2020 and subsequently named 'KLEPZ24810'. In July 2020 'KLEPZ24810' was first vegetatively propagated by vegetative stem cuttings in Stuttgart, Germany. 'KLEPZ24810' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Pink flowers with small markings;
2. Dark green leaves; and
3. Very weak leaf zonation.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany, in May 2024. The colors shown are as true as can be reasonably obtained by conventional photographic procedures.

DESCRIPTION OF THE NEW VARIETY

The following detailed descriptions set forth the distinctive characteristics of 'KLEPZ24810'. Data was collected on 12-week-old plants in Stuttgart, Germany under greenhouse conditions in March 2025. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium zonale* x *peltatum.*
*Common.*—*Pelargonium.*
*Designation.*—'KLEPZ24810'.

Parentage:
*Female parent.*—'PZ-2017-7461' (unpatented).
*Male parent.*—CALLIOPE® L Dark Red (patent status unknown).

Plant:
*Form*.—Bushy.
*Habit*.—Mounding.
*Height* (*from top of soil*).—16.0 cm.
*Width* (*horizontal plant diameter*).—21.0 cm.
*Natural flowering season*.—March to October.
*Propagation type*.—Vegetative by stem cuttings.
*Time to produce a finished flowering plant*.—12 weeks.
*Time to initiate and develop roots*.—4 weeks.
*Root description*.—Fine, dense, white, RHS 158A.
*Flower type*.—Zygomorphic.

Stems:
*Quantity of stems per plant*.—4 to 6.
*Color*.—RHS 144A.
*Surface texture*.—Pubescent.
*Stem form*.—Round.
*Diameter*.—1.0 cm.
*Length*.—4.0 cm to 7.0 cm.
*Internode length*.—1.0 cm.
*Anthocyanin*.—Absent.

Leaves:
*Arrangement*.—Alternate.
*Shape*.—Reniform.
*Apex*.—Round.
*Base*.—Open.
*Margin*.—Crenate.
*Surface texture both surfaces*.—Pubescent.
*Length*.—7.5 cm.
*Width*.—9.0 cm.
*Color*.—Upper surface: RHS 147A. Lower surface: RHS 147B.
*Zonation*.—Weak, distance to base 1.5 cm, distance to margin 2.0 cm.
*Zonation color*.—RHS N137B.
*Depth of sinus*.—3.0 cm.
*Petiole*.—Length: 4.5 cm. Diameter: 0.2 cm. Color: RHS 144A. Strength: Strong.
*Venation pattern*.—Palmate.
*Venation color*.—Upper surface: RHS 147A. Lower surface: RHS 144A.

Inflorescence:
*Lastingness of flowers on the plant*.—6 to 8 days.
*Umbels*.—Quantity of umbels per plant: 2 to 5. Length: 6.0 cm. Diameter: 9.0 cm.
*Individual florets of the umbel*.—Quantity of florets per umbel: 7 to 9. Depth: 1.5 cm. Diameter: 4.5 cm.
*Fragrance*.—Absent.

Flower buds:
*Cluster shape*.—Round.
*Cluster size*.—Length: 0.9 cm. Width: 1.2 cm.
*Surface texture*.—Pubescent.
*Bud*.—Height: 0.5 cm. Width: 0.4 cm. Shape: Round. Apex: Acute. Base: Obtuse. Margin: Entire. Color: RHS 144A.

Petals:
*Flower type*.—Double.
*Quantity per flower*.—7 to 10.
*Shape*.—Spatulate.
*Apex*.—Round.
*Base*.—Obtuse.
*Margin*.—Entire.
*Length*.—3.1 cm.
*Width*.—2.8 cm.
*Surface texture*.—Upper surface: Smooth. Lower surface: Smooth.
*Color of lobes*.—Upper lobes: Upper surface: Basic color RHS 73A, RHS NN155B at base, with markings and stripes of RHS N66B. Lower surface: RHS 75C. Lower lobes: Upper surface: Basic color RHS 73A, RHS NN155B at base, with markings of RHS N66B. Lower surface: RHS 75C.
*Markings*.—Present, upper petals single spot, 0.5 cm diameter and stripes, lower lobes single spot only.
*Conspicuousness of petal markings*.—Upper petals: Medium. Lower petals: Weak.

Petaloids:
*Quantity per flower*.—1 to 2.
*Shape*.—Crippled and deformed spatulate.
*Apex*.—Round.
*Base*.—Obtuse.
*Margin*.—Entire.
*Length*.—1.0 cm to 2.5 cm.
*Width*.—0.5 cm to 2.0 cm.
*Surface texture*.—Upper surface: Smooth. Lower surface: Smooth.
*Color*.—Upper surface: RHS 73A. Lower surface: RHS 75C.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Pubescent.
*Color*.—Upper surface: RHS 144A. Lower surface.—RHS 144A.
*Length*.—1.3 cm.
*Width*.—0.2 cm.
*Reflexing*.—Absent.

Pedicel:
*Length*.—2.5 cm.
*Diameter*.—0.2 cm.
*Color*.—RHS 183A.
*Surface texture*.—Pubescent.
*Strength*.—Medium.

Peduncle:
*Length*.—8.0 cm.
*Diameter*.—0.3 cm.
*Color*.—RHS 152A.
*Texture*.—Pubescent.
*Strength*.—Medium.

Reproductive organs:
*Stamens*.—Quantity per flower: 4 to 9. Anther length: 0.2 cm. Filament length: 0.6 cm. Filament color: RHS NN155D from base to middle, RHS 67A at tip. Pollen amount: Many or abundant. Pollen color: RHS 33B.
*Pistils*.—Number: 1.Stigma color: RHS 46B. Style length: 0.2 cm. Style color: RHS 46B. Ovary arrangement: Central. Ovary color: RHS 144A. Ovary diameter: 0.2 cm. Ovary length: 0.3 cm. Ovary Texture: Pubescent.

Fruit and seed set: None observed.

Disease and pest/insect resistance: None observed.

COMPARISON WITH PARENTAL LINES AND KNOWN VARIETY

'KLEPZ24810' is distinguished from its parents as described in Table 1.

TABLE 1

| Comparison with Parental Lines | | | |
|---|---|---|---|
| Characteristic | 'KLEPZ24810' | Female parent | Male parent |
| Flower color | Pink with small marking | Purple, pink with large marking | Dark red |
| Leaf color | Dark green | Dark green | Green |
| Leaf zonation | Very weak | Weak | Medium |

'KLEPZ24810' can be compared to the commercial variety Castello Benja Pink (patent status unknown). Differences between the two varieties are described in Table 2:

TABLE 2

| Comparison with Similar Variety | | |
|---|---|---|
| Characteristic | 'KLEPZ24810' | Castello Benja Pink |
| Flower Color | Pink with small marking | Pink with light pink center |
| Leaf zonation | Very weak | Medium |

I claim:

1. A new and distinct cultivar of *Pelargonium* Plant Named 'KLEPZ24810' as illustrated and described herein.

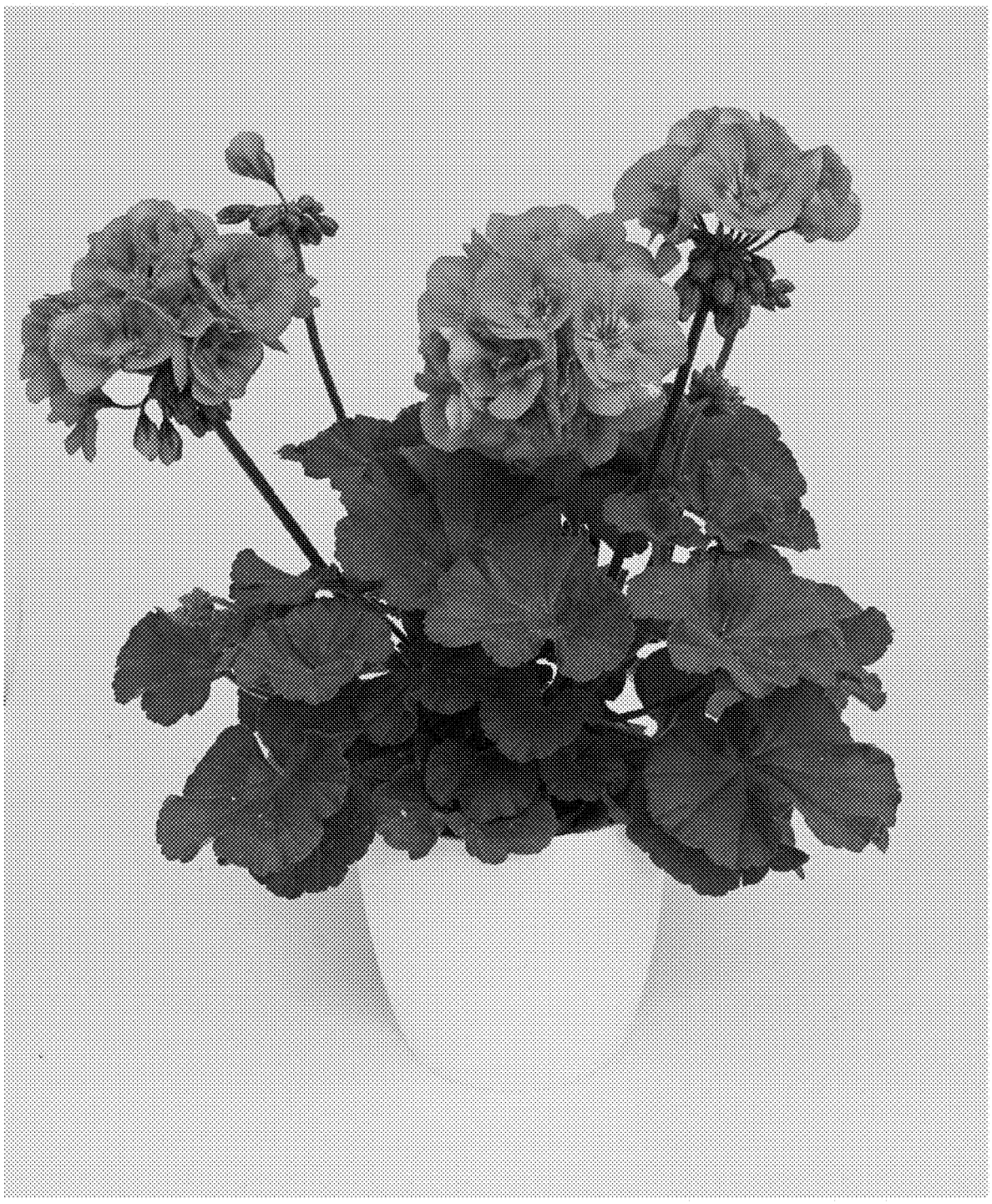

* * * * *